United States Patent [19]

Dragan

[11] 4,252,524
[45] Feb. 24, 1981

[54] FACE BOW FRAME

[76] Inventor: William B. Dragan, R.F.D. Burr St., Fairfield, Conn. 06430

[21] Appl. No.: 96,453

[22] Filed: Nov. 21, 1979

[51] Int. Cl.³ ............................................. A61C 19/04
[52] U.S. Cl. ...................................................... 433/73
[58] Field of Search ........................................... 433/73

[56] References Cited

U.S. PATENT DOCUMENTS 894,983   8/1908   Prothero ................................. 433/73
4,096,637   6/1978   Stide ...................................... 433/73

Primary Examiner—Robert Peshock
Attorney, Agent, or Firm—Arthur T. Fattibene

[57] ABSTRACT

A face bow frame to facilitate the occlusal restorations which can readily be adapted to the patient about either the arbitrary axis of rotation of the condyle or about the exact hinge axis of the center of rotation of the condyle and which face bow frame can be readily adapted to any of several different types of known articulators.

11 Claims, 7 Drawing Figures

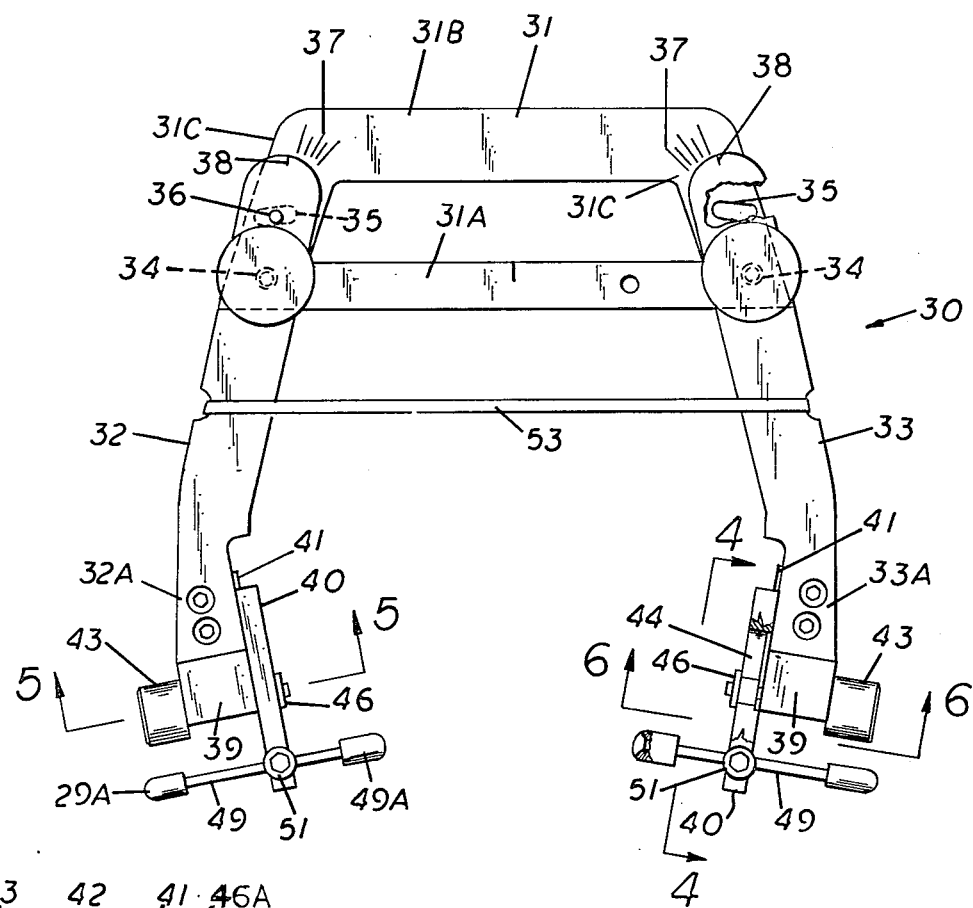

FACE BOW FRAME

RELATED PATENTS

This disclosure is directed to improvements in a face bow frame of a face bow assembly of a type disclosed in my prior U.S. Pat. No. 4,084,319 patented Apr. 18, 1978.

PROBLEM AND PRIOR ART

It was heretofore necessary for a dentist to simulate the mandible and maxilla relationship of a patient's jaw for reproducing the relative movements thereof to effect occlusal restorations. This is attained by utilizing a face bow to take an impression of one's bite relative to the orbital plane of the patient's head. The prior known face bows were constructed so as to be adapted to the patient's either about the arbitrary axis of the center of rotation where the ends of the face bow arms received in the depression anterior and medial to the tragi of a patient's ear; or about the exact hinge axis of the center of rotation of the condyle. The known face bow therefore were not adapted to be used interchangeably as to the use thereof relative to the arbitrary axis or the exact axis of the center of rotation of the condyle. For this reason, a dentist active in the practice of occlusal restorations had to maintain an inventory of differently constructed face bow assemblies as each such face bow was limited in use. Also, the face bows herefore known were specifically limited for use to a particular articulator. Thus, a face bow construction compatible with one type of articulator was not compatible to another articulator. The specific compatibility of a face bow construction to a particular articulator constituted a further limitation upon the use of a particular face bow construction.

OBJECTS

An object of this invention is to provide an improved face bow frame which can be optionally applied to a patient's face so as to be fitted either about an arbitrary axis or exact axis of the center of rotation of the condyle.

Another object is to provide an improved face bow frame which can be rendered readily adaptable for use on any of several of the well-known articulators.

Another object is to provide an improved face bow frame which a relatively simple in construction, positive in operation, and relatively inexpensive to manufacture.

BRIEF SUMMARY OF THE INVENTION

The foregoing objects, features and advantages are attained by a face bow frame having a pair of side arms which are pivotally mounted and which have connected to their respective free ends a mounting bracket. In one form of the invention, the mounting bracket is fixed so that the face bow frame is adapted to be hinged about the arbitrary axis of rotation. In another form the mounting bracket is adjustably connected so that the face bow frame can be hinged to a patient's face either about the exact hinge axis of the center of rotation of the condyle or the arbitrary axis of rotation. In either form, the mounting bracket is provided with a posterior and anterior aperture through which a mounting pin can be optionally disposed depending upon whether the face bow is to be hinged to a patient or an articulator. The apertures are arranged so that the face bow can be hinged to any of the well-known articulators by placing the mounting pin through the appropriate hole. A lock screw is associated with the apertures so as to lock the mounting pin when inserted in either hole.

FEATURES

A feature resides in a face bow frame in which the side arms have connected thereto a mounting bracket having predetermined spaced pin apertures whereby the face bow frame can be hinged to a patient's face and thereafter selectively hinged to any of the well-know articulators.

Another feature resides in adjustably connecting the mounting bracket to the ends of the side arms so that the face bow frame can be hinged either about the exact hinge axis of the center of rotation of the condyle or the arbitrary hinge axis.

Another feature resides in a face bow frame in which the side arms are normally biased toward one another.

Another feature resides in a face bow frame in which the side arms are pivotally adjusted and secured in an adjusted position with but a single lock screw.

Othere features and advantages will become readily apparent when considered in view of the drawings and specifications in which:

IN THE DRAWINGS

FIG. 3 is a plan view of a modified face bow frame construction.

FIG. 4 is a detail side view looking in the direction of line 4—4 on FIG. 3 showing the mounting bracket.

FIG. 5 is a detail sectional view taken along line 5—5 on FIG. 3.

FIG. 6 is a detail sectioned view taken along 6—6 on FIG. 3.

DETAILED DESCRIPTION

Figure 1:
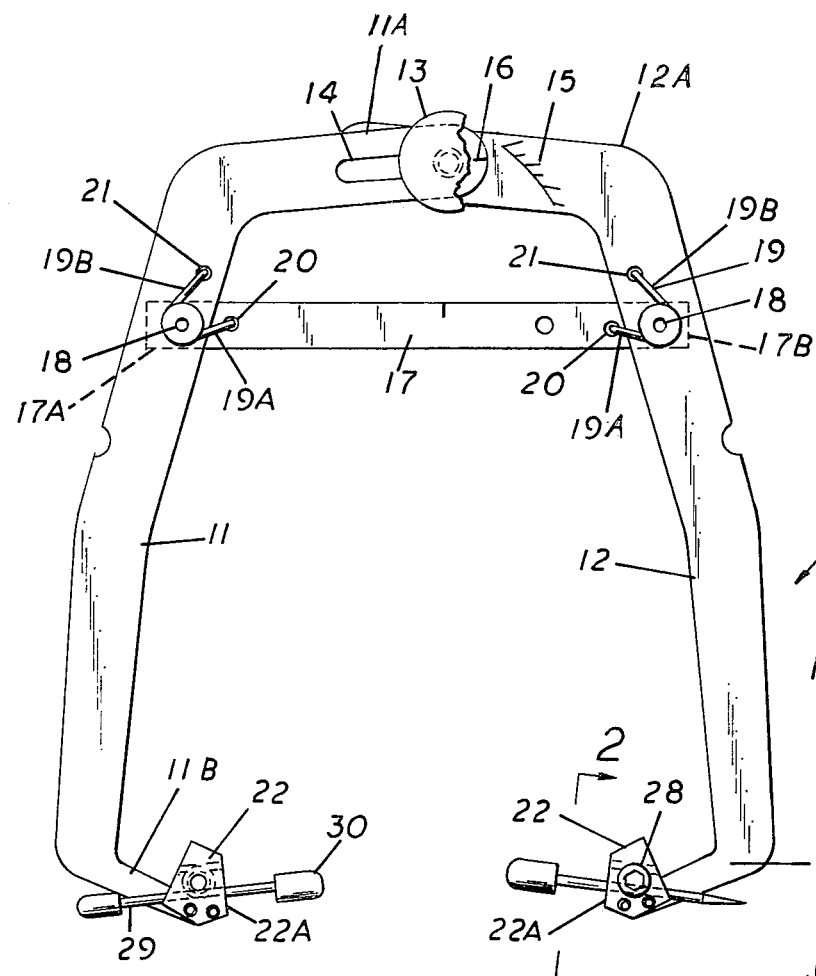
FIG. 1 illustrates plan view of a face bow frame embodying the present invention.
Figure 2A:
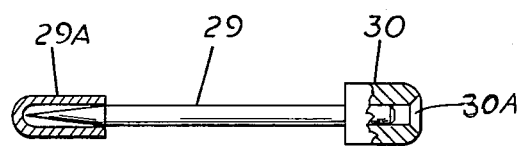
FIG. 2A is a detail view of a mounting pin for use with the face bow frame.
Figure 2:
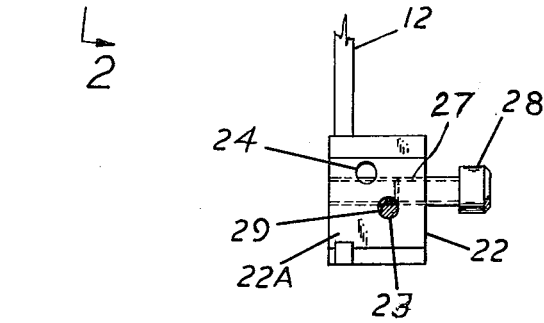
FIG. 2 is a detail end view of the mounting bracket looking along 2—2 on FIG. 1.

Referring to the drawings, there is shown in FIG. 1 and 2 a face bow frame 10 embodying the present invention. The illustrated face bow frame 10 comprises a pair of caliper or side arms 11 and 12 which have inwardly turned end portions 11A and 12B arranged to overly one another. A pivot lock screw 13 is provided about which the overlapping end portions 11A and 12A are pivotally connected. As best seen in FIG. 1, one of the inturned arm portions 11A is provided with an elongated slot 14. The inturned arm portion 12A of arm 12 is provided with a tapped hole for receiving the threaded shank of the pivot lock screw 13. It will, therefore, be apparent that when the lock screw or pivot 13 is loosened, the respective side arms 11 and 12 can be pivoted or adjusted with respect to one another whereby the face bow frame can be readily adapted or adjusted to a given patient. When the face bow 10 is properly fitted, the lock screw 13 is tightened and the arms are fixed relative to each other.

In the illustrated form of the invention, as seen in FIG. 1, a scale 15, which may be graduated in millimeters or in any other desirable units, is scribed onto one of the arms as for example side arm portion 12A. The end portion of the other side arm portion 11A is provided with a scribe or indicator mark 16. With the scale described, the arrangement is such that the intercondylar distance between the ear pieces, as will be hereinafter described can be readily determined, by taking a reading directly off scale 15.

Connected intermediate to the ends of the respective arms 11 and 12 is a cross piece 17. The respective ends 17A and 17B of the cross piece 17 are pivotally connected to the adjacent side arm by means of a pivot or rivet 18. A permanent spring 19 is provided for maintaining a spring bias on the respective side arms. Referring to FIG. 1, it will be noted that each pivot 18 is provided with a pigtail spring 19 wherein one end 19a of the spring 19 is anchored in an anchor hole 20 formed in the cross piece 17, and the other end 19b of the spring 19 is anchored in a hole 21 formed in the side arms. The arrangement of each spring 19 is such that the spring 19 will normally maintain a bias on its respective side arms which tends to pivot the free ends of the arms toward one another.

In this form of the invention, each of the side arms 11 and 12 has its free end turned inwardly, as indicated at 11B and 12B. Connected to the inturned free end of the respective side arms by any suitable means is an ear analogue or mounting bracket 22. As best seen in FIG. 1, the ear analogue or bracket 22 comprises a member having a face portion 22A. The faces 22A of the respective ear analogues are oppositely disposed. Each ear analogue or bracket 22 is provided with a pair of apertures 23 and 24 which extend therethrough. As best seen in FIG. 2, the posterior aperture 23 is offset at an angle of approximately 30 degrees with respect to the anterior aperture 24; and the anterior aperture 24 is located approximately 6 millimeters below the posterior aperture 23.

A combined stylus and ear plug pin 29 is adapted to be selectively inserted through either of the respective apertures 23, 24 as will be hereinafter described. In this form of the invention the posterior and anterior apertures 23 and 24 are predeterminately programmed relative to one another so that the posterior aperture 23 is used for receiving the combined stylus-ear plug pin 29 when the face bow frame 10 is used to take an ear-face bow recording; and the anterior aperture 24 can be used to mount the facebow onto certain types of anatomic articulators. For certain other articulators, the stylus-ear plus pin 29 can be maintained in the posterior aperture 23, and the ear plug 30 is used for mounting the face bow to such certain type of articulators.

To take an ear-facebow recording, the ear plug 30 connected to the end of the stylus or pin 29, which is extended through the posterior aperture, is disposed flush against the face 22A of the analogue or bracket 22. As noted in FIG. 2A, the ear plug 30 is provided with a center recess 30A which is arranged to receive the condylar mounts of a given articulator; when the face bow is hinged to such given articulator.

In order to secure the mounting pin 29 in fixed relationship relative to its mounting bracket regardless of which aperture 23 or 24 the mounting pin is disposed in, there is provided a securing means. The securing means comprises a tapped hole 27 which extends from top to bottom of the mounting bracket 22, as best noted in FIG. 2. The tapped hole 27 is arranged to extend between the posterior and anterior apertures 23 and 24 and communicates therewith. The arrangement is such that when said lock screw 28 is threaded into the tapped hole 27, it will engage the pin 29 regardless of which aperture pin 29 is disposed in. Also, it will be noted that because the tapped hole 29 is threaded from top to bottom of the mounting bracket 22, the lock screw 28 can be threaded into either end of the tapped hole to secure a pin 29 when disposed in either aperture 23 or 24.

The mounting pin comprises a stylus which has connected to one end thereof an ear plug 30 adapted to be received in the ear when the face bow frame 10 is to be fitted for an ear facebow recording. The other end of the pin protected by a cover 29A, is provided with a stylus point by which it can be mounted to certain types of articulators.

It will be understood that a toggle and bit fork assembly (Not Shown) is detachably connected to the cross bar or cross piece. Such toggle and bit fork assembly which is utilized with the described face bow frame 10 is similar to that disclosed in my U.S. Pat. No. 4,084,319; and therefore, need not be described in detail.

It will also be understood that a naseon gauge (also not shown) is suitably connected to the cross piece as described in my U.S. Pat. No. 4,084,319.

The side arms of the face bow frame 10, as shown in FIG. 1, it will be noted, can be readily adjusted and locked in the adjusted position simply by the tightening and loosening of one lock screw 13.

In operation, to take an ear-facebow recording, the bite fork (not shown) is covered with a wax or impression compound upon which the patient will bite in centrix relation. The face bow frame is then prepared by lining up the naseon gauge on the center line of the face bow frame to orient the facebow to the mid-saggital plane. The ear-plug stylus pin 29 is placed in the posterior hole 23 so that the ear plug 30 is flush against the face 22A of the analogue ear piece or bracket 22. With the side arms 11 and 12 loosened, the ear plugs 30 are guided into the patient's ears and the toggle is fitted to the stem of the bite fork whereupon the naseon guide is fitted and adjusted to the patient and locked. The lock nut or screw 13 is then tightened to fix the arms 11 and 12 relative to one another. The toggle assembly as described in my U.S. Pat. No. 4,084,319 is then tightened and secured to the stem of the bite fork. With the face bow frame thus fitted to the patient, the intercondylar distance can be readily read on the scale 15.

The face bow frame is removed from the patient by loosening the naseon and the lock pivot nut 13. The toggle assembly and the interocculusal recording or bite impression made is removed as an assembly, as described in my U.S. Pat. No. 4,084,319 and put aside together with the intercondylar reading until the laboratory phase is to be performed.

In the laboratory the toggle assembly with the interocclusal recording is remounted to another face bow, as described, in preparation of mounting the casts to an articulator. The face bow of the present invention is arranged so that it can be readily adapted to any of several different types of articulators, thereby rendering the face bow frame 10 adaptable to any of the popular articulators which a dentist or laboratory may have. For example, with the ear piece or plug located in the posterior hole or aperture 23, the ear plug 23 forms a trunion for receiving the mounting rods of certain types of articulators, e.g. those types of articulators wherein the center of their condyler simulate an hinge axis coinciding to that of an ear-facebow recording. When using other types of articulators e.g. the kind which mount their face bows to simulate an exact hinge axis of rotation about their condyle mounts, an offset of the ear-facebow recording must be made. Therefore, to adapt the face bow frame 10 described for use with these latter types of articulators, it is only necessary to remove the ear plug stylus or pin 29 from the posterior hole 23 and insert the pin 19 through the anterior aperture 24. The pin 19 is so constructed that the end adapted to be attached to the condylar mounts of the given articulator is located so as to complement either the pin or hole of the condylar mount of the articulator. Thus, depending upon the condylar mount of the articulator, the stylus end of the pin 19 is used where the condylar mount is a hole and the ear plug end of the pin 19 is used when the condylar mount of the articulator is a hole. In either event, locating the pin 19 in the anterior aperture compensates the offset ear facebow recording when the face bow is utilized on those articulators which mount their face bows on the center of their condyles.

For the foregoing, it will be noted that the face bow frame 10, when used for an ear facebow reading, is rendered readily adapted for use with either an articulator that hinge its face bow about the ear axis or the exact center of their condyle. The face bow is then rendered universal in application to various articulators.

FIG. 3 illustrates a modified form of facebow frame 30. The face bow frame 30 of FIG. 3 is constructed so that the frame can be optionally used by the dentist as a transfer bow to take either an ear oriented face bow recording or an exact hinge axis recording. Referring to FIG. 3, the face bow frame 30 comprises a fixed base member 31 which includes a pair of spaced apart cross sections 31A and 31B interconnected by an opposed spaced apart end portions 31C-31C. Thus as shown in FIG. 3, the fixed base member comprises a generally integrally formed D shaped member.

Connected to the respective end portions 31C-31C of the base member 31 are side arms 32 and 33. The respective side arms 32 and 33 are pivotally connected to the end portions 31C of the base member 31 for movement relative thereto. As shown, the pivot means comprises a headed stud or screw 34 which has a threaded shank which extends through a hole formed on the respective side arms 32 and 33 and which screw shank is threaded into a tapped hole formed in the base member 31. Thus, when the lock screw 34 is loosened, the respective side arms can be individually adjusted or pivoted about there lock screw pivot 34.

To secure the side arms 32 and 33 in a pivoted adjusted position, the lock screw 34 need only to be hand tightened.

To limit the range of the pivoting movement of the respective side arms 32 and 33, the base member 31 is provided with a slot 35 located intermediate to the end of the end portions 31C-31C. Slot 35 accommodates a stop pin 36 connected to the respected arms. The stop pin 36 and slot 35 thus cooperates to define the limit or range between which the respective side arms can be pivoted relative to the base member.

In order to determine the left or right condylar distance relative to the center line of a patient's face, an appropriate scale 37 is formed on the rear cross section 31B of the base member 31 and adjacent to the end of the respective side arms 32 and 33. An indicating mark 38 is located on the ends of the respective side arms 31 and 32. Thus, when either the left or right side arms is required to be adjusted with respect to a patient's face, the left and right condylar distance to either side of center can be readily noted by the position of the indicator 38 relative to the graduated scale 37.

The respective free ends 32A and 33A of the respective side arms 32 and 33 has connected thereto a mounting block 39 to which an analogue ear piece or mounting bracket 40 is connected.

Referring to FIG. 3, the mounting block 40 is formed with a rail or guide 41 which extends longitudinally along the respective side arm 31 or 32 and has a transverse opening 42 formed therein for receiving a locking screw 43. The mounting bracket 40 comprises an elongated member which is provided with a longitudinally extending slot 44 formed therein. As shown, the outer longitudinal side surface 40A of the mounting bracket 40 is provided with a keyway or recess 45 which is adapted to receive or slide on the rail 41 formed on the mounting block 39. The arrangement is such that the locking screw 43 will extend through the elongated slot 44 with the end of the screw 43 being threaded into a flanged locking nut 46. The lock nut 46 is provided with a threaded boss 46A extended through the slot 44 of the mounting bracket to receive the screw 43. Accordingly, as seen in FIG. 4, it will be noted that the mounting bracket 40 is longitudinally adjusted relative to the side arms within a range indicated by the length of the longitudinally extending slot 44.

It will also be apparent that when the locking screw 43 is loosened, the mounting bracket 40 can be rendered longitudinally and rotatably adjustable about the locking screw 43.

In the extreme outer end portion of the mounting bracket 40, there is provided a posterior aperture 47 and anterior aperture 48. As described with respect to the embodiment of FIG. 1, the apertures 47 and 48 are offset at an angle of approximately 30 degrees wherein the anterior aperture 48 is located approximately 6 millimeters below the posterior aperture 47. A combined stylus and ear plug pin 49 is provided, and it is arranged to be selectively positioned either in the posterior hole 47 or the anterior hole 48 depending upon the particular type of articulator the face bow 30 is to be mounted to.

The longitudinally and rotatably arranged analogue ear piece or mounting bracket 40 enables a dentist to utilize the face bow construction 30 as described with respect to FIG. 1 for taking either an ear-face bow recording or the face bow 30 can be optionally used to take a face bow recording about the exact hinge axis of rotation about the center of the condyle; as will be hereinafter described.

In order to fix the mounting pin 49 in either position, when located in either the anterior or posterior aperture, the mounting bracket 40 is provided with a tapped hole 50 extending normal thereto and located between the posterior and anterior apertures 47 and 48. As hereinafter described, the tapped opening 50 is disposed in communication with a portion of the posterior and anterior apertures. The arrangement is such that when the mounting pin is located in either of the apertures, a lock screw 51 threaded into the tapped opening will frictionally secure the pin 49 in the adjusted position regardless of which aperture the pin is located. Also, it will be apparent that by extending the tapped opening 50 through the opposed ends of the mounting bracket 40, the lock screw 51 can be inserted through either end of the tapped hole 50 for effectively locking the mounting pin in either aperture. It will be understood that a toggle and bite fork assembly and naseon gauge as described in my U.S. Pat. No. 4,084,319 is adapted to be connected to the cross piece portion 31A of the base member.

The mounting pin 49 comprises an elongated pin which is provided with a stylus point on one end and an ear plug 49A on the other end, similar to that shown on FIG. 2A.

As shown in FIG. 2A; the ear plug 49A, is also provided with a center depression which may also be utilized for receiving the pin mounts of a particular articulator. Thus, depending upon whether the condular mounts of a particular articulator is provided with mounting pins or with mounts adapted to receive a mounting pin, that the mounting pins 49 of face bow frame construction 30 can be reversed so as to render the face bow readily adapted to either type of condular mounts which are commonly used by known face bow articulators.

In order to maintain the side arms 32 and 33 of the face bow frame normally biased toward one another, an elastic or rubber band 53 may be provided as indicated.

In lieu of such biasing rubber band, it will be understood that the side arms of the face bow frame 30 may also be biased by a spring similar to that described with respect to the face bow 10 of FIG. 1.

From the foregoing description, it will be apparent that the face bow construction 30 of FIG. 3 can be used to take an ear-facebow recording in a manner similar to that described in FIG. 1. In using the face bow construction 30 of FIG. 3 to take an ear-facebow recording, the analogue ear pieces or bracket 40 is fully extended and firmly locked in parallel relationship to the adjacent side arm. The combined ear plug and stylus pin 49 is locked in the posterior hole 47 with the end of the plug 49A flush against the inside surface of the bracket 40. The face bow 40 is then fitted to the patient as hereinbefore described, with the ear plugs located in the patient ears. With the face bow 30 of FIG. 3, the left and right condylar distance from the mid-saggital plane are read on the scales 37 and recorded.

After the ear-facebow recording has been made, the recording can be transferred and the casts mounted to an articulator in a manner described with respect to FIG. 1. That is, the face bow can be readily hinged to those articulators which have their face bows hinged about an approximate axis of rotation of the condyle by maintaining the pin 49 in its posterior hole 47. For use of the facebow 30 on articulators that mount their face bows directly on the center of their condyles, the mounting pin 49 is inserted into the posterior hole 48 to compensate for the offset of the ear face bow recording. Depending upon the condylar mounts of a particular articulator, the pin 49 can be oriented in its aperture to complement the condylar mounts of the articulator.

In using the face bow frame 30 for an exact hinge axis transfer, the hinge axis of the patient is established by any desired method. One of the simpler methods to locate the patient's hinge axis by palpating the center of the glenoid fossa when the mouth is fully open. When the center is found, it is marked. When the exact center has been marked, the face bow 30 is applied to the patient in a manner similar to that described for taking an ear-facebow recording.

Once the ear face bow recording has been completed, and before the face bow is removed from the patient, the respective analogue ear pieces or brackets are one at a time repositioned so that the stylus end of the respective pins 49 point toward the skin and at the point marked on the patient which indicates the exact hinge center. This is accomplished by loosening one of the arms, and reversing the pin to extend the stylus through the posterior hole 47. The analogue ear piece is also loosened and rotated to locate the stylus opposite the marked center on the patient. With the pin stylus opposite the marked center, the bracket lock screw 43 is tightened. The other arm and associated bracket and stylus is similarly adjusted on the other side.

With the face bow 30 thus adjusted and with all lock screws tightened, the face bow 30 is removed from the patient. The hinge axis recording thus removed from the patient is ready for mounting. The face bow 30 can be readily attached to the articulator by placing the stylus end of the pin 49 into the indentation in the center of the condyle.

Using the face 30 as a simple ear oriented facebow transfer, the face bow can be adapted to any of several different articulators as hereinbefore described.

While the foregoing invention has been described with respect to several embodiments thereof, it will be readily understood and appreciated that variations and modifications may be made without departing from the spirit or scope of the invention.

What is claimed is:

1. A face bow frame comprising a pair of relatively movable arms, each of said arms having a free end, means for securing said movable arms in a fixed position relative to one another, means acting on said arm for maintaining a biasing force on said arms, mounting means connected to each of said free end of said respective arms, said mounting means including a mounting bracket and a mounting pin; each said mounting brackets having an anterior aperture and a posterior aperture formed therein, said anterior aperture being below and angularly disposed relative to said posterior aperture, said pin being adapted to be received in either of said apertures and securing means for fixedly securing said pin in adjusted position when inserted in either of said apertures.

2. A face bow frame as defined in claim 1 wherein said securing means includes a tapped hole disposed normal to and between said anterior and posterior apertures, said hole being opened to each of said apertures and a lock screw thread into said hole to frictionally secure said mounting pin when located in either of said apertures.

3. A face bow frame as defined in claim 2 wherein said tapped holes extends through said mounting bracket whereby said lock screw can be threaded through either end of said tapped hole.

4. A face bow frame as defined in claim 1 wherein each arm having inturned overlapping end portions, means for adjustably connecting said overlapping end portion, said means including an elongated slot formed on the inturned end of one arm, and a pivot connected to the inturned end of the other arm, said pivot extending through said elongated slot, a cross piece interconnected between said arms intermediate to the ends thereof; pivot means connecting the ends of said cross piece to said arms whereby said arms are free to pivot relative to said cross piece about said pivot means, and a spring means operating on said arms for biasing said arms relative to said cross piece.

5. A face bow as defined in claim 4 wherein said spring means includes a pigtail spring having one end anchored to said cross piece and having the other spring end anchored to said arm.

6. A face bow frame as defined in claim 1 wherein said mounting pin having an ear plug connected to one end which is adapted to be received in a patient's ear when said frame is placed on the patient's face, and the other end of said mounting pin being adapted to be received in the condylar mounts of a given articulator.

7. A face bow construction as defined in claim 1 and including means for connecting said mounting bracket for longitudinal and angular adjustment relative to its respective arm whereby said face bow frame can be fitted to the exact hinge axis of the center of the rotation of the condyle.

8. A face bow construction as defined in claim 7 wherein said bracket includes a slot whereby said bracket is longitudinally and angularly adjustable relative to its respective arm, and pivot lock means for securing said bracket in the longitudinally and/or angularly adjusted position relative to its connected arm.

9. A face bow frame adapted to be fitted to a patient's face about the hinge axis of the center of rotation of the condyle comprising: a base member, a side arm connected to each end of said base member, means for pivoting each of said side arms to its respective end of said base member whereby each of said side arms is independently pivoted relative to said base member, a bracket connected to the free end of each arm, said bracket having means for longitudinally and angularly adjusting said bracket relative to its respective arm, said adjusting means includes a locking pivot for connecting said bracket to its respective arm for longitudinally and augular rotation; and said bracket having an elongated slot for receiving said locking pivot, and a locking nut co-operatively associated with said locking pivot to lock said bracket in its adjusted position, said bracket each having a posterior and anterior hole extending there through, said anterior hole being disposed below and angularly offset relative to said posterior hole, a mounting pin adapted to be inserted into one of said holes, means for fixedly securing said mounting pin in one of said holes, and means for normally biasing said arms relative to each other.

10. A face bow frame as defined in claim 9 wherein said base member comprises a pair of spaced apart cross members having intergrally connected end portions, said side arms being connected to one of said cross members, and limiting means co-operatively associated with said base member and each of said side arms to limit the relatively pivoting movement between each of said arms and base member.

11. A face bow frame as defined in claim 9 wherein said fixedly securing means for securing said mounting pin comprises a tapped hole, said tapped hole extending through said mounting bracket normal to and between the respective anterior and posterior holes, said tapped hole disposed in communication with said anterior and posterior holes, and a lock screw threaded into said tapped hole to frictionally secure said pin when located in either of said posterior or anterior holes.

* * * * *